(12) United States Patent
Haun et al.

(10) Patent No.: US 10,722,540 B1
(45) Date of Patent: Jul. 28, 2020

(54) MICROFLUIDIC DEVICE AND METHOD FOR SHEAR STRESS-INDUCED TRANSFORMATION OF CELLS

(71) Applicant: THE REGENTS OF THE UNIVERSITY OF CALIFORNIA, Oakland, CA (US)

(72) Inventors: Jered Haun, Irvine, CA (US); Alan Widgerow, Irvine, CA (US); Derek Banyard, Orange, CA (US); Xiaolong Qiu, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 525 days.

(21) Appl. No.: 15/421,206

(22) Filed: Jan. 31, 2017

Related U.S. Application Data

(60) Provisional application No. 62/289,883, filed on Feb. 1, 2016.

(51) Int. Cl.
| | |
|---|---|
| *B01L 3/00* | (2006.01) |
| *G01N 1/28* | (2006.01) |
| *C12M 1/33* | (2006.01) |
| *A61K 35/35* | (2015.01) |
| *C12N 5/077* | (2010.01) |
| *A61K 9/00* | (2006.01) |

(52) U.S. Cl.
CPC ............ *A61K 35/35* (2013.01); *A61K 9/0019* (2013.01); *C12N 5/0653* (2013.01)

(58) Field of Classification Search
None
See application file for complete search history.

(56) References Cited

U.S. PATENT DOCUMENTS

| | | | |
|---|---|---|---|
| 4,883,763 | A | 11/1989 | Holen et al. |
| 8,080,380 | B2 | 12/2011 | Chee |
| 2002/0142470 | A1 | 10/2002 | Clarke et al. |
| 2004/0137607 | A1 | 7/2004 | Tanaami et al. |
| 2005/0138567 | A1 | 6/2005 | Smith et al. |
| 2006/0223178 | A1 | 10/2006 | Barber |
| 2007/0025876 | A1 | 2/2007 | Nishijima et al. |
| 2007/0025930 | A1 | 2/2007 | Rico-Lattes et al. |
| 2007/0026416 | A1 | 2/2007 | Fuchs |
| 2007/0026426 | A1 | 2/2007 | Fuchs |
| 2007/0092876 | A1 | 4/2007 | Xu |
| 2009/0014360 | A1 | 1/2009 | Toner et al. |
| 2009/0098541 | A1 | 4/2009 | Southern |
| 2009/0155877 | A1 | 6/2009 | Illiescu |
| 2010/0081189 | A1 | 4/2010 | Zantl et al. |
| 2010/0190265 | A1 | 7/2010 | Dufva et al. |
| 2011/0085950 | A1 | 4/2011 | Lee et al. |
| 2012/0100521 | A1 | 4/2012 | Soper |
| 2013/0149724 | A1 | 6/2013 | Chander |
| 2013/0295598 | A1 | 11/2013 | Marx et al. |
| 2014/0057311 | A1 | 2/2014 | Kamm et al. |
| 2014/0120537 | A1 | 5/2014 | Chang |
| 2014/0248621 | A1 | 9/2014 | Collins |
| 2014/0377866 | A1 | 12/2014 | Haun et al. |
| 2015/0231244 | A1 | 8/2015 | Chi et al. |
| 2015/0285785 | A1 | 10/2015 | Hahn |
| 2015/0285786 | A1 | 10/2015 | Hahn et al. |
| 2015/0377861 | A1 | 12/2015 | Pant et al. |
| 2016/0047735 | A1 | 2/2016 | Grisham et al. |
| 2017/0131187 | A1 | 5/2017 | Haun et al. |
| 2018/0106805 | A1 | 4/2018 | Allen |

FOREIGN PATENT DOCUMENTS

| | | |
|---|---|---|
| AU | 2013216683 B2 | 9/2007 |
| CA | 2609361 A1 | 11/2006 |
| CA | 2327789 C | 9/2007 |
| CA | 2760574 A1 | 11/2010 |
| CA | 2799901 A1 | 11/2011 |
| CA | 2924883 A1 | 3/2015 |

(Continued)

OTHER PUBLICATIONS

Bassaneze et al., "Shear Stress Induces Nitric Oxide-Mediated Vascular Endothelial Growth Factor Production in Human Adipose Tissue Mesenchymal Stem Cells", Stem Cells and Development, 2010, vol. 19, No. 3, pp. 371-378. (Year: 2010).*
Topcu et al., "Increasing the Viability of Fat Grafts by vascular Endothelial Growth Factor", Arch Facial Plast Surg, 2012, 14(4), pp. 270-276. (Year: 2012).*
Alharbi et al., "Conventional vs. micro-fat harvesting: How fat harvesting technique affects tissue-engineering approaches using adipose tissue-derived stem/stromal cells", Journal of Plastic, Reconstructive & Aesthetic Surgery (2013), vol. 66, pp. 1271-1278. (Year: 2013).*
Office Action dated May 8, 2018 in U.S. Appl. No. 15/413,201, (20pages).
Office Action dated Sep. 6, 2017 in U.S. Appl. No. 15/413,201, (12pages).

(Continued)

*Primary Examiner* — Laura Schuberg
(74) *Attorney, Agent, or Firm* — Vista IP Law Group LLP (57) ABSTRACT

A method of processing a lipoaspirate sample includes mechanically processing the lipoaspirate sample to generate nanofat. The nanofat is then input into a microfluidic device comprising a plurality of serially arranged stages comprising one or more microfluidic channels having a plurality of expansion and constriction regions extending along the length of the one or more microfluidic channels, wherein each subsequent stage of the plurality has an increasing number of microfluidic channels of decreasing dimensions. The nanofat is flowed through the plurality of serially arranged stages in a plurality of cycles to generate sheared nanofat. The sheared nanofat is then collected after flowing through the plurality of serially arranged stages. The sheared nanofat may then be injected and/or applied to the subject. In an alternative embodiment, filtered or mechanically processed lipoaspirate may be run through the microfluidic device.

18 Claims, 8 Drawing Sheets

(56) References Cited

FOREIGN PATENT DOCUMENTS

| | | |
|---|---|---|
| CA | 162188 S | 1/2016 |
| CA | 2963468 A1 | 4/2016 |
| CA | 2572113 C | 4/2017 |
| CA | 2609361 C | 11/2017 |
| CN | 101443023 A | 5/2009 |
| CN | 106434542 A | 1/2010 |
| CN | 201389496 Y | 1/2010 |
| CN | 102458302 A | 5/2012 |
| CN | 102002478 B | 1/2013 |
| CN | 102861105 A | 1/2013 |
| CN | 103038333 A | 4/2013 |
| CN | 104630139 A | 5/2015 |
| CN | 105934155 A | 9/2016 |
| CN | 106834121 A | 6/2017 |
| DK | 1778834 T3 | 11/2010 |
| DK | 1778833 T3 | 6/2011 |
| DK | 1885382 T3 | 6/2011 |
| DK | 1599575 T3 | 1/2012 |
| DK | 1778834 T5 | 1/2012 |
| DK | 1921133 T3 | 8/2015 |
| DK | 1638507 T3 | 6/2017 |
| DK | 1670315 T3 | 8/2017 |
| DK | 2571975 T3 | 10/2017 |
| DK | 3046417 T3 | 10/2017 |
| EP | 2145951 A1 | 1/2010 |
| EP | 2145952 A1 | 1/2010 |
| EP | 1778833 B1 | 3/2011 |
| EP | 1885382 B1 | 3/2011 |
| EP | 2332555 A3 | 6/2011 |
| EP | 2343360 A1 | 7/2011 |
| EP | 2305276 A3 | 9/2011 |
| EP | 2308963 A3 | 9/2011 |
| EP | 2371943 A1 | 10/2011 |
| EP | 1778834 B9 | 11/2011 |
| EP | 1599575 B9 | 3/2012 |
| EP | 2348103 A3 | 7/2012 |
| EP | 2571975 A2 | 3/2013 |
| EP | 1743021 B1 | 3/2014 |
| EP | 1778293 B1 | 4/2015 |
| EP | 1776126 B1 | 5/2015 |
| EP | 1921133 B1 | 5/2015 |
| EP | 2980206 A1 | 2/2016 |
| EP | 2617427 B1 | 8/2016 |
| EP | 3046417 A4 | 9/2016 |
| EP | 3106511 A1 | 12/2016 |
| EP | 2422622 B1 | 1/2017 |
| EP | 1638507 B1 | 3/2017 |
| EP | 1670315 B1 | 4/2017 |
| EP | 2571975 B1 | 7/2017 |
| EP | 3046417 B1 | 7/2017 |
| EP | 2574663 B1 | 8/2017 |
| EP | 2380970 B1 | 12/2017 |
| EP | 3106512 B1 | 3/2018 |
| EP | 3299451 A1 | 3/2018 |
| EP | 2465923 B1 | 4/2018 |
| ES | 2364957 T3 | 9/2011 |
| ES | 2364689 T3 | 2/2012 |
| ES | 2373551 T3 | 2/2012 |
| ES | 2545385 T3 | 9/2015 |
| ES | 2633604 T3 | 9/2017 |
| ES | 2641547 T3 | 11/2017 |
| ES | 2649387 T3 | 1/2018 |
| HK | 1078009 A1 | 6/2011 |
| HK | 1096424 A1 | 2/2013 |
| HK | 1165261 A1 | 8/2015 |
| HR | P20171471 T1 | 11/2017 |
| JP | 2008278821 A | 11/2008 |
| JP | 2008278822 A | 11/2008 |
| JP | 2009-75067 | 4/2009 |
| JP | 2009189280 A | 8/2009 |
| JP | 2009189281 A | 8/2009 |
| JP | 2009189282 A | 8/2009 |
| JP | 2009269930 A | 11/2009 |
| JP | 2010032444 A | 2/2010 |
| JP | 2010043876 A | 2/2010 |
| JP | 2010075066 A | 4/2010 |
| JP | 2010075114 A | 4/2010 |
| JP | 2010095531 A | 4/2010 |
| JP | 2010127620 A | 6/2010 |
| JP | 2010127708 A | 6/2010 |
| JP | 2010148450 A | 7/2010 |
| JP | 2010148451 A | 7/2010 |
| JP | 2011010615 A | 1/2011 |
| JP | 2011010616 A | 1/2011 |
| JP | 2012051923 A | 3/2012 |
| JP | 2012075439 A | 4/2012 |
| JP | 2012149088 A | 8/2012 |
| JP | 2014031389 A | 2/2014 |
| JP | 05960689 B2 | 8/2016 |
| JP | 2016136956 A | 8/2016 |
| JP | 06208787 B2 | 10/2017 |
| JP | 2018030815 A | 3/2018 |
| KR | 2005109941 A | 11/2005 |
| KR | 2006025180 A | 3/2006 |
| KR | 2006030861 A | 4/2006 |
| KR | 2007002058 A | 1/2007 |
| KR | 2007017974 A | 2/2007 |
| KR | 2007038538 A | 4/2007 |
| KR | 2007089254 A | 8/2007 |
| KR | 779812 B1 | 11/2007 |
| KR | 2008017389 A | 2/2008 |
| KR | 811995 B1 | 3/2008 |
| KR | 2008103611 A | 11/2008 |
| KR | 930139 B1 | 12/2009 |
| KR | 2010029272 A | 3/2010 |
| KR | 1083454 B1 | 11/2011 |
| KR | 2012003961 A | 1/2012 |
| KR | 2012020143 A | 3/2012 |
| KR | 1127305 B1 | 4/2012 |
| KR | 2012038534 A | 4/2012 |
| KR | 1145508 B1 | 5/2012 |
| KR | 1150666 B1 | 7/2012 |
| KR | 1197909 B1 | 11/2012 |
| KR | 2013038412 A | 4/2013 |
| KR | 1278437 B1 | 6/2013 |
| KR | 1310578 B1 | 9/2013 |
| KR | 1400544 B1 | 5/2014 |
| KR | 2016055827 A | 5/2016 |
| KR | 2017115296 A | 10/2017 |
| KR | 2017115377 A | 10/2017 |
| MX | 2011011402 A | 2/2012 |
| MX | 2016003127 A | 10/2016 |
| WO | WO2003024215 A1 | 3/2003 |
| WO | WO2003053346 A2 | 7/2003 |
| WO | WO2003053362 A2 | 7/2003 |
| WO | WO2005012480 A2 | 2/2005 |
| WO | WO2006014156 A1 | 2/2006 |
| WO | WO20060175980 A1 | 7/2006 |
| WO | WO2006069349 A9 | 9/2006 |
| WO | WO2006039129 A8 | 12/2006 |
| WO | WO2007061530 A1 | 5/2007 |
| WO | WO2007139551 A1 | 12/2007 |
| WO | WO2008060466 A3 | 8/2008 |
| WO | WO2008013863 A3 | 10/2008 |
| WO | WO2008140046 A1 | 11/2008 |
| WO | WO2006112941 B1 | 12/2008 |
| WO | WO2006127007 A3 | 4/2009 |
| WO | WO2009055610 A1 | 4/2009 |
| WO | WO2009076548 A1 | 6/2009 |
| WO | WO2008140044 A8 | 8/2009 |
| WO | WO2009101910 A1 | 8/2009 |
| WO | WO2010021993 A1 | 2/2010 |
| WO | WO2010035709 A1 | 4/2010 |
| WO | WO2010073808 A1 | 7/2010 |
| WO | WO2010124235 A1 | 10/2010 |
| WO | WO2010127310 A1 | 11/2010 |
| WO | WO2011145075 A2 | 11/2011 |
| WO | 2012/139209 A1 | 10/2012 |
| WO | WO2013144883 A2 | 10/2013 |
| WO | WO2013144883 A3 | 11/2013 |
| WO | WO2014016750 A1 | 1/2014 |
| WO | WO2014064642 A1 | 5/2014 |
| WO | WO 2014/130391 | 8/2014 |

(56) References Cited

FOREIGN PATENT DOCUMENTS

| WO | WO2015042182 A1 | 3/2015 |
|---|---|---|
| WO | WO 2015/127126 | 8/2015 |
| WO | WO2015120388 A1 | 8/2015 |
| WO | WO2015140737 A1 | 9/2015 |
| WO | WO2016007434 A1 | 1/2016 |
| WO | WO2016054592 A1 | 4/2016 |
| WO | WO2017100328 A1 | 6/2017 |
| WO | WO2017115289 A1 | 7/2017 |
| WO | WO2017125159 A1 | 7/2017 |
| WO | WO2017195156 A1 | 11/2017 |

OTHER PUBLICATIONS

Restriction Requirement dated Jun. 1, 2017 in U.S. Appl. No. 15/413,201, (5pages).
Office Action dated Feb. 23, 2017 in U.S. Appl. No. 15/413,201, (10pages).
Kim, M. Y. et al., Microfabrication of High-Resolution Porous Membranes for Cell Culture, J. Memb. Sci. 452, 460-469 (2014).
MACS Miltenyi Biotec, gentleMACSTM Dissociator, The gentle way of automated tissue dissociation, gentlemacs.com (2pages), 2010.
Banyard, Derk A. et al., Phenotypic Analysis of Stromal Vascular Fraction after Mechanical Shear Reveals Stress-Induced Progenitor Populations, Pastic and Reconstructive Surger, Aug. 2016, vol. 138, No. 2, Shear Stress Progenitor Morphogenesis, www.PRSJournal.com, 237e-247e.
Bianchi, Francesca et al., A New Nonenzymatic Method and Device to Obtain a Fat Tissue Derivative Highly Enriched in Pericyte-Like Elements by Mild Mechanical Forces From Human Lipoaspirates, Cell Transplantation, vol. 22, pp. 2063-2077, 2013.
Conde-Green, Alexandra et al., Effects of Centrifugation on Cell Composition and Viability of Aspirated Adipose Tissue Processed for Transplantation, Aesthetic Surgery Journal, 30(2) 249-255 (2009).
Conde-Green, Alexandra et al., Influence of decantation, washing and centrifugation on adipocyte and mesenchymal stem cell content of aspirated adipose tissue: A comparative study, Journal of Plastic, Reconstructive & Aesthetic Surgery (2010) 63, 1375-1381.
Heneidi, Saleh et al., Awakened by Cellular Stress: Isolation and Characterization of a Novel Population of Pluripotent Stem Cells Derived from Human Adipose Tissue, PLOS ONE, www.plosone.org, Jun. 2013, vol. 8, Issue 6, e64752 (14pages).
Tonnard, Patrick et al., Nanofat Grafting: Basic Research and Clinical Applications, Plastic and Reconstructive Surgery, Oct. 2013, vol. 132, No. 4, Nanofat Grafting, www.PRSJournal.com, 2013.
Office Action dated Mar. 26, 2019 in U.S. Appl. No. 15/413,201, (21pages).
Interview Summary dated Jul. 14, 2019 in U.S. Appl. No. 15/413,201, (3pages).
PCT International Preliminary Report on Patentability (Chapter I of the Patent Cooperation Treaty) for PCT/US2017/036429, Applicant: The Regents of the University of California, Form PCT/IB/326 and 373, dated Dec. 20, 2018 (14pages).
Notice of Preliminary Rejection (non-final) dated Mar. 21, 2019 for Korean Patent Application No. 10-2019-7000183, Applicant: The Regents of the University of California (19pages).
Office Action dated Feb. 8, 2019 in U.S. Appl. No. 16/101,254, (46pages).
Office Action dated Oct. 31. 2018 in U.S. Appl. No. 16/101,254, (32pages).
Amendment and Response dated Jan. 29, 2019 in U.S. Appl. No. 16/101,254, (19pages).
Final Office Action dated Feb. 8, 2019 in U.S. Appl. No. 16/101,254, (46pages).
Request for Continued Examination and Response dated Apr. 18, 2019 in U.S. Appl. No. 16/101,254, (19pages).
Response to Office Action dated Jul. 26, 2019 in U.S. Appl. No. 15/413,201, (19pages).
Adams, Andre A. et al., Highly Efficient Circulating Tumor Cell Isolation from Whole Blood and Label-Free Enumeration Using Polymer-Based Microfluidics with an Integrated Conductivity Sensor, J Am Chem Soc., Jul. 9, 2008; 130(27): 8633-8641. doi:10.1021/ja8015022.
Final Office Action dated Sep. 5, 2018 in U.S. Appl. No. 15/413,201, (18 pages).
Office Action dated Mar. 26, 2019 in U.S. Appl. No. 15/413,201, (17 pages).
Final Office Action dated Aug. 7, 2019 in U.S. Appl. No. 15/413,201, (52 pages).
Notice of Allowance and Issue Fee dated Feb. 7, 2020 in U.S. Appl. No. 15/413,201, (18 pages).

* cited by examiner

MICROFLUIDIC DEVICE AND METHOD FOR SHEAR STRESS-INDUCED TRANSFORMATION OF CELLS

RELATED APPLICATION

This Application claims priority to U.S. Provisional Patent Application No. 62/289,883 filed on Feb. 1, 2016, which is hereby incorporated by reference in its entirety. Priority is claimed pursuant to 35 U.S.C. § 119 and any other applicable statute.

TECHNICAL FIELD

The technical field generally relates to devices and methods for applying shear stress to live cells (and/or tissue) and in particular microfluidic-based devices for applying shear stress to living cells to induce phenotypic changes and/or enrichment in the cells.

BACKGROUND

A topic at the forefront of plastic surgery research is addressing the variability experienced when transferring fat from one location to another to fill soft tissue defects (i.e., fat grafting). Cell-assisted lipotransfer (CAL) is a technique used in reconstructive and aesthetic medicine that involves the addition of the stromal vascular fraction (SVF) to fat grafts, and has resulted in significant improvements in fat graft retention. Typically, the SVF is harvested from adipose tissue by a short digestion step using the enzyme collagenase. Recently, a technique called 'nanofat grafting' was developed, whereby standard lipoaspirate is homogenized by manually passing it vigorously between two connected syringes, and then reinjecting the homogenized lipoaspirate in human patients for the correction of superficial rhytides and pigmentation. For example, Tonnard et al. disclosed improved skin quality when nanofat was used to correct superficial rhytides, scars, and dark lower eyelids. Tonnard et al., Nanofat grafting: basic research and clinical applications, Plast. Reconstr. Surg., 132(4), pp. 1017-26 (2013). Unfortunately, the current process of generating nanofat is limited by poor control of hydrodynamic shear forces and subject to user-dependent variability which is not ideally suited for clinical environments. Poor control of hydrodynamic shear forces may adversely affect cell viability and the ability to promote shear-stress induced transformation of cells.

SUMMARY

According to one embodiment, a method of applying shear stress to live cells involves running live cells (obtained from lipoaspirate) through a microfluidic device having a series of microfluidic channels that include repeating expansion/constriction patterns to induce fluid shear forces on the cells that are passed through the microfluidic channels of the device. In one embodiment, the device contains an inlet, an outlet, and a branching microfluidic channel array located between the inlet and outlet. The branching microfluidic channels include the repeating expansion/constriction patterns. The branching microfluidic channels in the microfluidic device are arranged in a number of serially arranged stages with each stage (in the downstream direction) having an increasing number of channels of reduced dimension. For example, a first stage may include a single microfluidic channel having repeating expansion and constriction regions. This first stage proceeds to a second stage that has multiple microfluidic channels (e.g., two (2)) of reduced dimension (e.g. width) with each having repeating expansion and constriction regions. The second stage then proceeds to a third stage that has multiple microfluidic channels (e.g., four (4)) of reduced dimension (e.g. width) with each having repeating expansion and constriction regions. This third stage then proceeds to a fourth stage that has multiple microfluidic channels (e.g., four (8)) of reduced dimension (e.g. width) with each having repeating expansion and constriction regions. Thus, in this particular embodiment, each stage results in a doubling in the number of microfluidic channels. This doubling in the number of microfluidic channels may be accompanied by a reduction in the width dimension of the microfluidic channel by about one-half. Thus, while each successive stage of the microfluidic device has a doubling in the number of microfluidic channels, each microfluidic channel is reduced in width by half.

Various modifications of the above scheme may be made to the microfluidic device. For example, there may be fewer stages or more stages. Further, rather than have the number of microfluidic channels double after each stage, the number of microfluidic channels may triple, quadruple, or the like. Similarly, at each successive stage, the width does not have to be reduced by half as it could be reduced by some other amount. Further, while the width is described as being reduced, the reduction in dimension of the microfluidic channels in successive stages could include the height as well depending on the orientation of the expansion and constriction regions.

In one particular embodiment, the final or last stage of the device may have a minimum distance within the range of about 200 µm to about 600 µm. The microfluidic channel may have a height that is typically within the range of about 200 to about 500 µm and stays uniform throughout the device. Larger channel dimensions may be used because dissociating the fat tissue all the way down to single cells may damage or even kill the stem cells that we are seeking to stimulate/enrich using the applied mechanical stress.

In one embodiment, an optional filter module is placed directly downstream (or in an alternative embodiment upstream of) of the microfluidic device to filter the processed sample. The filter module may be integrated directly after the microfluidic device for rapid and efficient processing. The filter module may include a nylon filter membrane with pore size of about 500 µm that is sandwiched between layers of PDMS that are patterned using photolithograpy. Other materials such as metal, polymer, cellulose, and the like may be used instead of nylon. This filter membrane only allows lipoaspirate tissue or cells that are smaller than the cutoff diameter to pass through. In still another alternative embodiment, the optional filter module is located upstream of the microfluidic device (e.g., upstream of the inlet to the microfluidic device but downstream with respect to the syringe).

In another embodiment, a method of processing a lipoaspirate sample includes mechanically processing the lipoaspirate sample to generate nanofat. The nanofat is then input into a microfluidic device comprising a plurality of serially arranged stages comprising one or more microfluidic channels having a plurality of expansion and constriction regions extending along the length of the one or more microfluidic channels, wherein each subsequent stage of the plurality has an increasing number of microfluidic channels of decreasing dimensions. The nanofat is flowed through the plurality of serially arranged stages in a plurality of cycles to generate sheared nanofat. The sheared nanofat is then collected after flowing through the plurality of serially arranged stages.

In another embodiment, a method of transforming fat cells from a subject includes obtaining a lipoaspirate sample from the subject containing the fat cells and removing connective tissue from the lipoaspirate sample using filtering or mechanical processing. The filtered lipoaspirate is then input into a microfluidic device comprising a plurality of serially arranged stages comprising one or more microfluidic channels having a plurality of expansion and constriction regions extending along the length of the one or more microfluidic channels, wherein each subsequent stage of the plurality has an increasing number of microfluidic channels of decreasing dimensions. The lipoaspirate is flowed through the plurality of serially arranged stages in a plurality of cycles to generate sheared lipoaspirate. The sheared lipoaspirate is then collected after flowing through the plurality of serially arranged stages.

In another embodiment, a method of transforming fat cells from a subject includes mechanically processing a lipoaspirate sample obtained from the subject sample to generate nanofat and inputting the nanofat into a microfluidic device comprising a plurality of serially arranged stages comprising one or more microfluidic channels having a plurality of expansion and constriction regions extending along the length of the one or more microfluidic channels, wherein each subsequent stage of the plurality has an increasing number of microfluidic channels of decreasing dimensions. The nanofat is flowed through the plurality of serially arranged stages in a plurality of cycles to generate sheared nanofat. The sheared nanofat is then collected after flowing through the plurality of serially arranged stages.

The innovative microfluidic-based method can be used to reproduce, with better results and reliability, the shear force environment of nanofat shearing. The microfluidic device enables, for example, an automated and consistent method of mechanical stress processing which has the potential to be used in the clinic to enhance fat grafting procedures among other autologous therapies. The microfluidic device allows for well-defined and enhanced fluid shear stresses to be applied to lipoaspirate samples, leading to stronger activation and/or enrichment of stem cell populations. Integration of the optional filter module will also result in a single platform in which SVF can be harvested, processed, and the resulting sample administered directly to a patient without further manipulation. This will be critical for clinical applications. It can be adapted to fit within a larger device comprising a series of the microfluidic devices allowing for delivery of a sufficient volume of regenerative multipotent cells. In some embodiments, the device may be divided into one section that cleans, filters, and delivers material for traditional fat grafting, while the other section utilizes this microfluidic platform to deliver the concentration of regenerative cells. Both may be combined for cell assisted lipotransfer or they may be used separately for various indications.

DETAILED DESCRIPTION OF ILLUSTRATED EMBODIMENTS

Figure 1A:
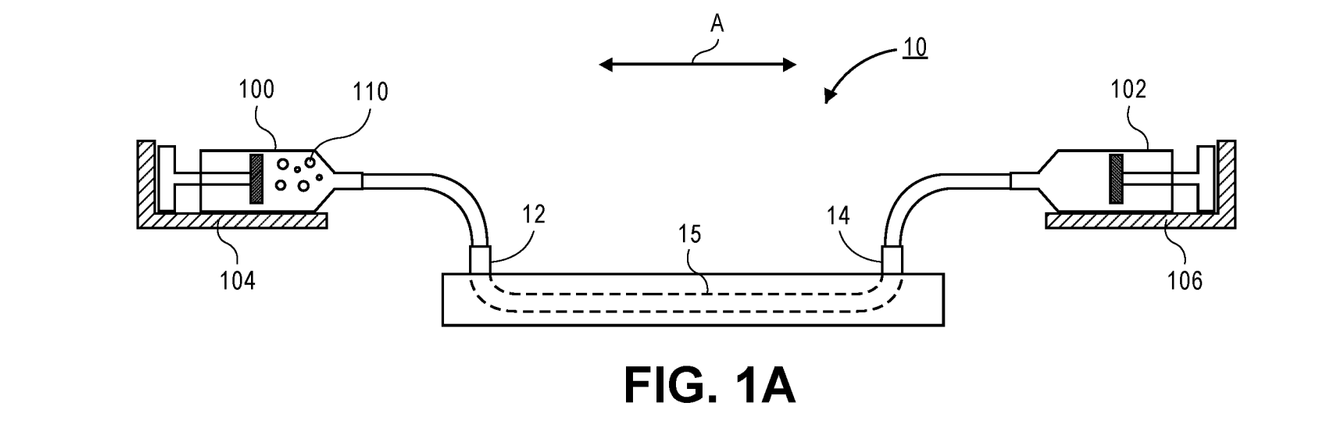
FIG. 1A illustrates a schematic representation of the microfluidic device being used to process nanofat according to one embodiment.

FIG. 1A illustrates a microfluidic device 10 according to one embodiment. The device includes an inlet 12, outlet 14, and a branching microfluidic channel array 15 located between the inlet 12 and outlet 14. Also illustrated in FIG. 1A are two syringes 100, 102 that are mounted in respective syringe pumps 104, 106 that are used, in one particular embodiment, to pump nanofat 110 back-and-forth in direction of arrow A through the microfluidic device 10 for processing. As used herein, the term "nanofat" refers to lipoaspirate that has been mechanically pre-processed. The nanofat 110 may be created from the lipoaspirate by passing standard lipoaspirate which has been obtained from a subject in a liposuction (object subject to optional wash) procedure back and forth between two syringes (not shown) that are secured to one another with a Luer coupling or the like. Alternatively, the nanofat 110 may be mechanically pre-processed in other ways such as by passing the lipoaspirate through a strainer or mechanical filter. In this regard, in one embodiment, standard lipoaspirate or macrofat is first converted to nanofat 110. The nanofat 110 is then loaded into syringe 100 which can then be processed using the microfluidic device 10 as described herein.

In the embodiment illustrated in FIG. 1A, the nanofat 110 is pumped using pump 104 from the syringe 100 and into the inlet 12 of the microfluidic device 10. As explained in further detail below, the microfluidic device 10 contains several microfluidic channels 18, 24, 26, 30 (seen in FIG. 1C) arranged in successively arranged stages with each stage of the microfluidic device having an increasing number of microfluidic channels 18, 24, 26, 30 of decreased dimensions. Further, each microfluidic channel 18, 24, 26, 30 of each stage contains a plurality of expansion regions 20 and constriction regions 21 extending along the length thereof. The serial stages of microfluidic channels 18, 24, 26, 30 and the expansion regions 20 and constriction regions 21 impart shear stress on the nanofat 110 in a consistent and reproducible manner. In the embodiment of FIG. 1A, the nanofat 110 exits the microfluidic device 10 via the outlet 14 and enters into the syringe 102. This represents a single cycle or pass through the microfluidic device 10. The processed (single cycle) nanofat 110 in the syringe 102 is then flowed back through the microfluidic device 10 (using pump 106) in the reverse direction whereby the nanofat 110 exits via the inlet 12 and enters the syringe 100. The cycle then proceeds again, whereby the pump 104 pumps the nanofat 110 from the syringe 100 and into the inlet 12 of the microfluidic device 10. The nanofat 110 encounters the plurality of expansion regions 20 and constriction regions 21 in each of the stage and exits the microfluidic device 10 via the outlet 14 and enters the syringe 102. This represents two (2) cycles through the microfluidic device 10.

In an alternative embodiment, the second pump 106 may be omitted and the output that exits the outlet 14 may be recirculated back to the inlet 12 to complete additional passes or cycles through the microfluidic device 10. For example, a peristaltic-type pump could recirculate the nanofat 110 through the microfluidic device 10 for multiple cycles.

Figure 1B:
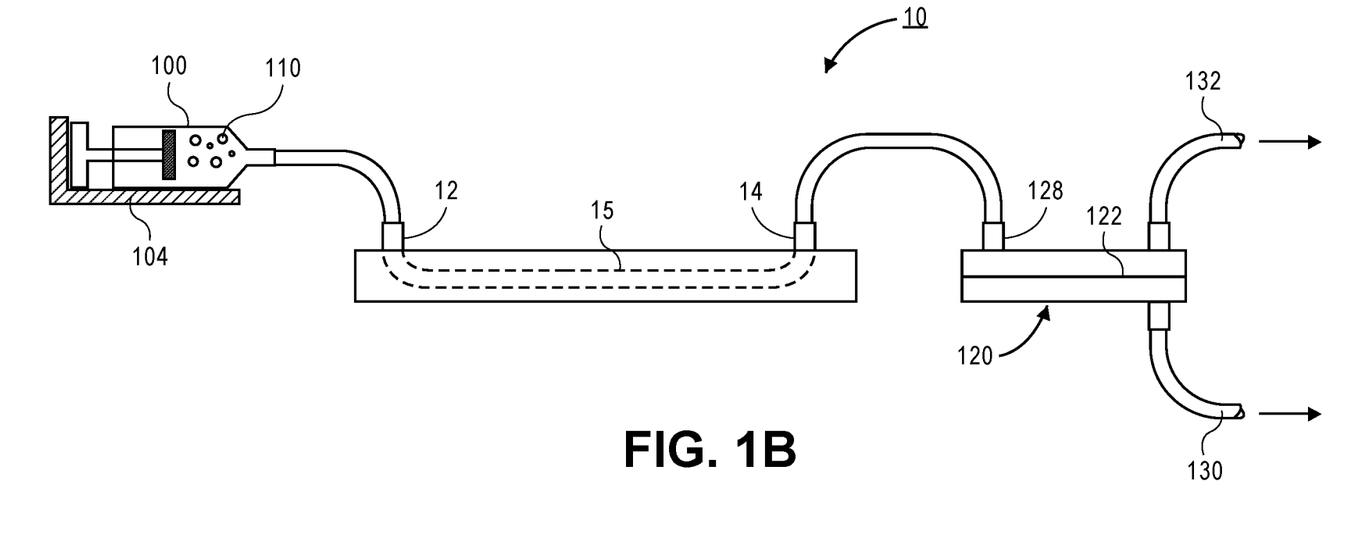
FIG. 1B illustrates a schematic representation of the microfluidic device according to another embodiment being used to process nanofat.
Figure 1C:
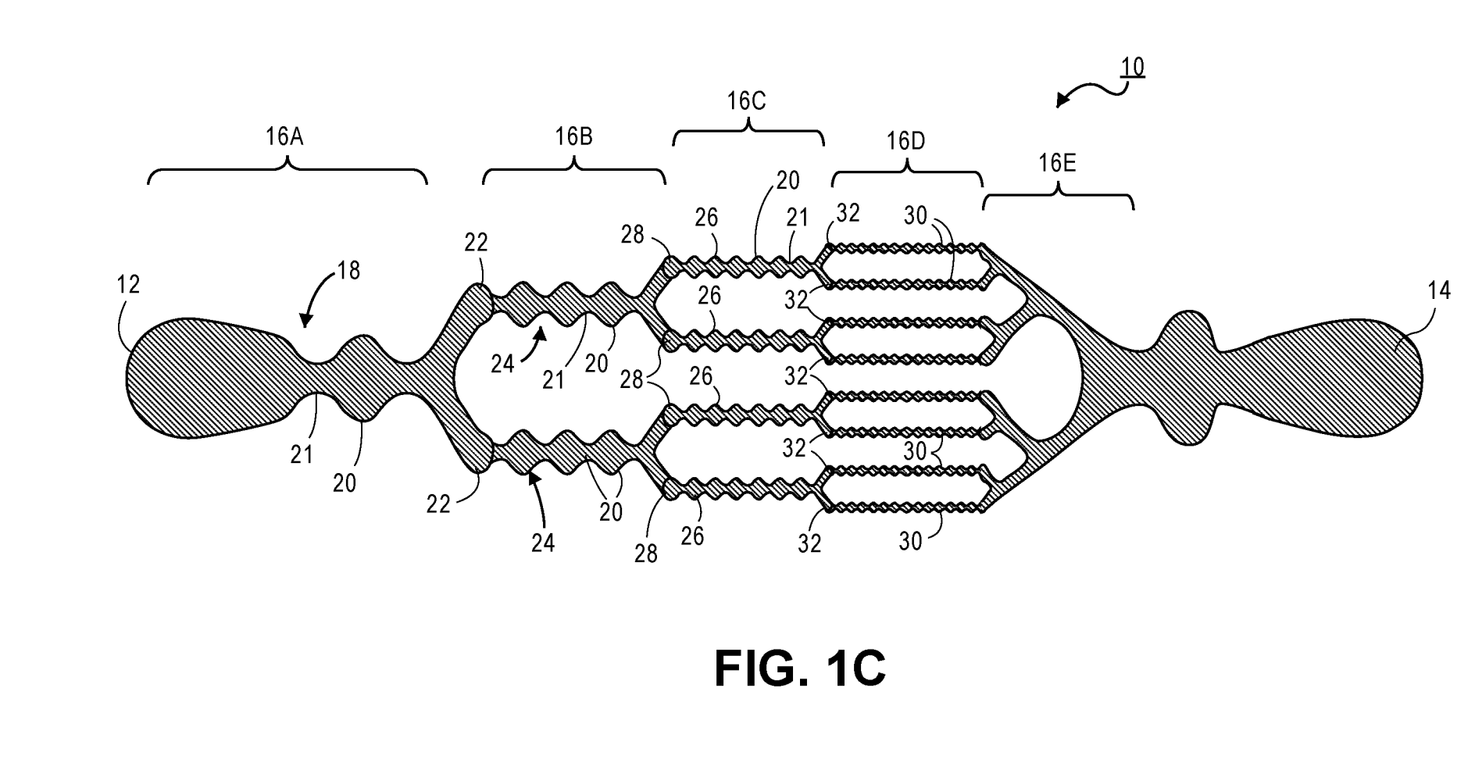
FIG. 1C illustrates one embodiment of a microfluidic device with four stages.
Figure 1D:
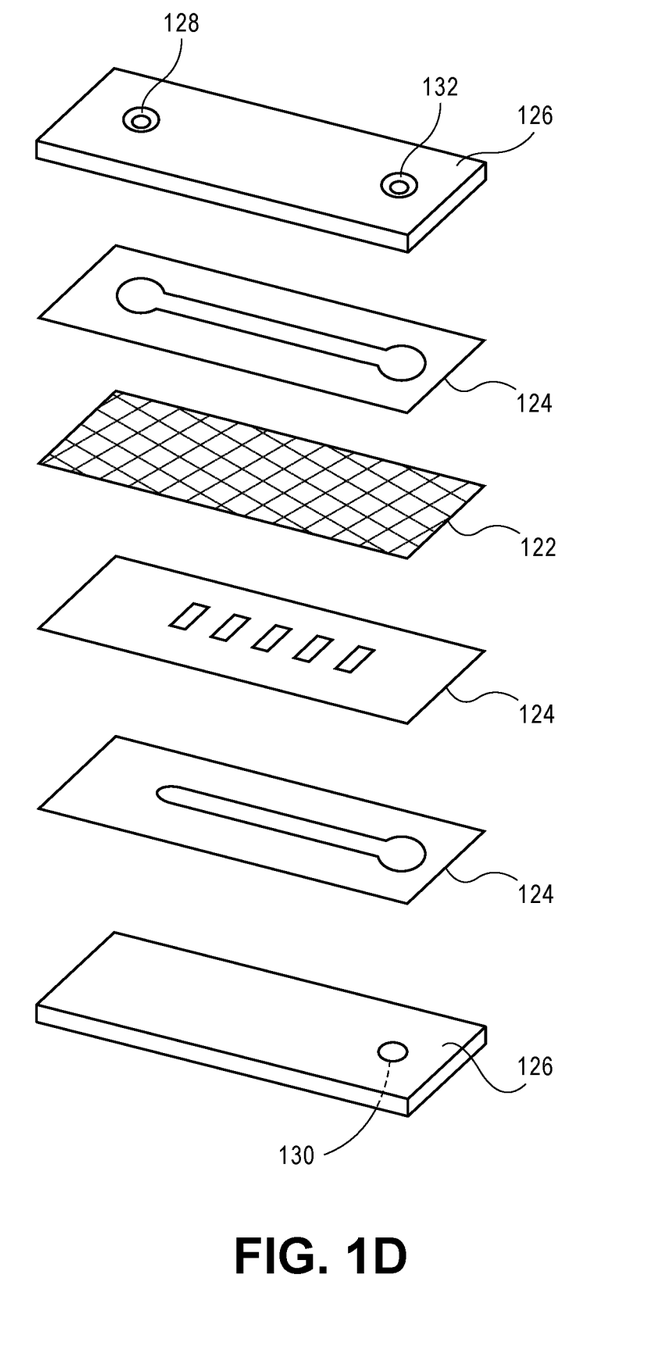
FIG. 1D illustrates an exploded view of a filter module according to one embodiment.

FIG. 1B illustrates the microfluidic device 10 according to another embodiment of the invention. In this embodiment, a downstream filter module 120 is coupled to the outlet 14 of the microfluidic device 10. The filter module 120 includes a filter membrane 122 with pore size of ~500 μm that is sandwiched between layers 124 of PDMS that are patterned using photolithograpy as seen in FIG. 1D. The outermost layers 126 of the filter module 120 may be made of a plastic material such as polyethylene terephthalate (PET) and include an inlet 128 and two outlets 130, 132. This filter membrane 122 only allows lipoaspirates smaller than its cutoff diameter to go through the filter membrane 122 and exiting via outlet 130 while removing large aggregates that exit the filter module via outlet 132. The fluid that exits from either outlet 130, 132 can optionally be recycled back into the microfluidic device 110 for further hydrodynamic treatment. Also, either the output from outlet 130, 132 can be sent to a further device downstream of the filter module 120. In still another alternative embodiment, the filter module 120 may be added or switched in-line with the output of the microfluidic device 10. For example, the configuration of FIG. 1A may be used to perform multiple cycles on the nanofat 110. After the desired number of cycles have been completed, the output could be switched through a filter module 120 such as that illustrated in FIG. 1B.

In another alternative embodiment, the filter module 120 is located upstream with respect to the microfluidic device 10. For example, the filter module 120 would be located downstream of the syringe 100 but upstream of the microfluidic device 10. In one particular embodiment, the filter module 120 may include a filter medium or filtering structure that is used to remove connective tissue or larger-sized tissue matter. The filter medium or filtering structure may include mechanical obstructions or the like that disrupt the lipoaspirate sample into smaller-sized clusters of cells or cell populations while retaining the bulky connective tissue (e.g., collagen). In this particular example, rather than run nanofat 110 through the microfluidic device 10, the filtered lipoaspirate may be directly run through the microfluidic device 10.

Figure 2:
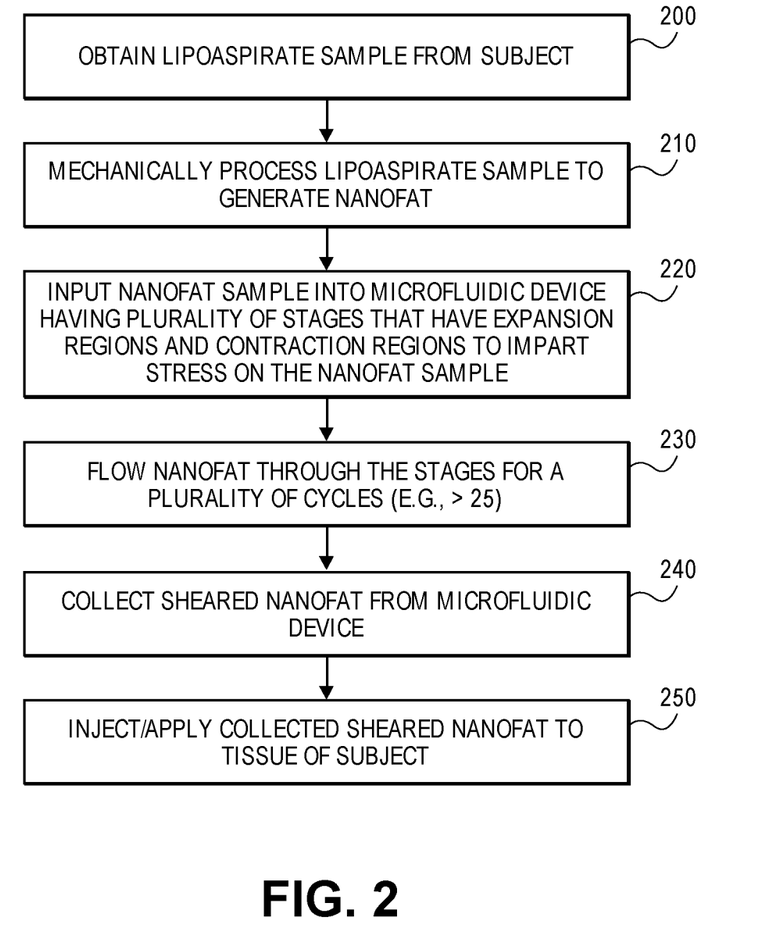
FIG. 2 illustrates a flowchart of an exemplary method of processing a lipoaspirate sample obtained from a mammalian subject (e.g., human).

In this embodiment, with reference to FIG. 2, operation 210 is omitted entirely and lipoaspirate is directly input into the microfluidic device. The process continues as illustrated in FIG. 2 with the difference being that lipoaspirate is flowed through the microfluidic device 10 instead of nanofat 110. One concern with processing lipoaspirate directly is that the microfluidic device 10 will clog due the larger, connected nature of raw lipoaspirate; however, appropriate mechanical disruption or filtering may also permit lipoaspirate to be run through the microfluidic device 10 without having to first create nanofat 110.

The microfluidic device 10 is preferably made from multiple layers which are laminated together to form the completed microfluidic device 10. For example, hard plastic such as polyethylene terephthalate (PET) can be laser cut into desired patterns and then aligned in a stack and fused together using intermediate adhesive layer(s) and pressure lamination. The hard plastic format is more robust than alternatives produced using photolithography and polydimethyl siloxane (PDMS). In a separate embodiment, the device may be made as a single layer using a 3D printer.

Referring back to FIG. 1C, the microfluidic device 10 includes an inlet 12 and an outlet 14 as well as plurality of serially connected stages 16A, 16B, 16C, 16D formed within the microfluidic device 10 and located between the inlet 12 and the outlet 14. The first stage 16A of the microfluidic device 10 includes a single microfluidic channel 18 this is connected at an upstream side to the inlet 12 and contains therein a plurality of expansion regions 20 and constriction regions 21 therein. The expansion regions 20 and constrictions regions 21 are formed within the microfluidic channel 18 and are alternating regions where the width of the channel 18 increases and decreases. The smallest or minimum width dimension of the microfluidic channel 18 occurs between two opposing constriction regions 21. Generally, this minimum distance is within the range of about 200 μm to about 600 μm. The expansion regions 20 and constrictions regions 21 generate fluidic jets of varying size scales and magnitudes to hydrodynamically shear the sample. The flow-through format enables rapid processing and is ideal for connecting to downstream fluidic operations.

In one embodiment, the expansion regions 20 and constriction regions 21 are a continuous expansion and constriction of the channel width. This will modulate fluid velocity, actively mixing the sample and generating shear forces across tissue and cell aggregates. The expansion regions 20 and constriction regions 21 are connected by smooth curved lines, resulting in relatively gradual velocity changes to avoid that turbulent mixing and recirculating flows. In one embodiment, the maximum width in the expansion region is 3-fold greater than the minimum width in the constriction, and this ratio is maintained throughout the microfluidic device 10. In this embodiment, the constriction regions are separated by a distance equal to the expansion region width. This results in an increase in the number of constrictions per channel through the device 10. While the expansion regions 20 and the constriction regions 21 are oriented along with width of the microfluidic device 10 these could also be oriented along the height direction.

The second stage 16B is connected to the downstream end of the first stage 16A at the end of microfluidic channel 18. The second stage 16B may be located in a different layer of the microfluidic device 10 than the first stage 16A whereby the second stage 16B is connected to the first stage 16A using a vias 22. The second stage 16B includes a plurality of microfluidic channels 24 with each microfluidic channel 24 having a plurality of expansion regions 20 and constriction regions 21 formed therein. In addition, the dimensions of the microfluidic channels 24 within the second stage 16B are narrowed as compared to the microfluidic channel 18 of the first stage 16A. In one aspect of the invention, the second stage 16B includes two microfluidic channels 24 wherein the width of each channel 24 is reduced by a factor of about x/2 where x represents the minimum width of the microfluidic channel 18 of the first stage 16A. The height of the microfluidic channels 18, 24 remains the same. The height may vary but is generally within the range of about 200 to about 500 µm.

Still referring to FIG. 1C, a third stage 16C is connected to the end of the second stage 16B. The third stage 16C includes four microfluidic channels 26 with pairs of microfluidic channels 26 connecting to the downstream end of the microfluidic channels 24. The interface between the end of the second stage 16B and the beginning of the third stage 16C may be accomplished through vias 28. In one aspect of the invention, the third stage 16C includes four microfluidic channels 26 wherein the minimum width of each microfluidic channel 26 is reduced by a factor of about x/4 where x represents the minimum width of the microfluidic channel 18 of the first stage 16A. The third stage 16C may be located in a different layer of the device 10 from the upstream second stage 16B.

A fourth stage 16D is connected to the end of the third stage 16C. The fourth stage 16D includes eight microfluidic channels 30 with pairs of microfluidic channels 30 connecting to the downstream end of the microfluidic channels 26. The interface between the end of the third stage 16C and the beginning of the fourth stage 16D may be accomplished through vias 32. In one aspect of the invention, the fourth stage 16D includes eight microfluidic channels 30 wherein the minimum width of each microfluidic channel 30 is reduced by a factor of about x/8 where x represents the minimum width of the microfluidic channel 18 of the first stage 16A. Thus, if the minimum width of the first stage 16A is 2 mm then the minimum width of the fourth and final stage 16D is 250 µm (2 mm to 1 mm to 500 µm to 250 µm). If the minimum width of the first stage 16A is 4 mm then the minimum width of the fourth and final stage 16D is 500 µm (4 mm to 2 mm to 1 mm to 500 µm). The multiple acrylic layers of the microfluidic device 10 may be secured together via fasteners such as screws or the like. Alternatively, the various layers may be bonded to one another.

While the microfluidic device 10 described herein has four stages 16A, 16B, 16C, 16D fewer or more stages can be used. Further, while each successive set of microfluidic channels located in a downstream stage is described as having a minimum width that is about one-half the minimum width of the immediately upstream microfluidic channels, other fractions are contemplated (e.g., ¼, ⅓, etc.). In addition, in the embodiment illustrated in FIG. 1C, the number of downstream microfluidic channels doubles as compared to the prior upstream stage. In other embodiments, the number of microfluidic channels may be a higher multiple of two (e.g., 3×, 4×, etc.).

FIG. 2 illustrates a flowchart of an exemplary method of processing a lipoaspirate sample obtained from a mammalian subject (e.g., human). In operation 200, a lipoaspirate sample (e.g., macrofat) is obtained from the subject. The lipoaspirate contains live cells therein. This lipoaspirate sample may be obtained using conventional fat harvesting techniques that are well known to those skilled in the art. Typically, this lipoaspirate sample may be obtained by performing liposuction or body sculpting on the subject. In a liposuction procedure, a surgical tool such as a cannula that has holes or apertures therein is used to extract fat from tissue regions of the subject. This extracted fat or lipoaspirate sample is collected and used for the mechanical processing operation 210. The extracted fat or lipoaspirate may optionally be washed in a saline or buffer solution prior to mechanical processing in operation 210.

In the mechanical processing operation 210, the lipoaspirate is converted to nanofat 110. Mechanical processing may involve vigorously passing the lipoaspirate back-and-forth between two connected syringes (connected via Luer connector or tubing). Mechanical processing may also include, in addition to or as an alternative to syringe-to-syringe processing, straining or even filtration of the lipoaspirate to remove connective tissue. Next, as seen in operation 220, the nanofat 110 is then input into the microfluidic device 10 described herein that has the plurality of stages that impart shear stress on the sample using the plurality of expansion regions 20 and contraction regions 21.

In the example illustrated in FIGS. 1A and 1B, the nanofat 110 is input and flowed through the microfluidic device 10 using the pumps 104, 106. In certain embodiments, these may be syringe-based pumps or they may include peristaltic pumps. By flowing the nanofat 110 through the microfluidic device 10, the nanofat 110 is subject to shear forces due to the expansion regions 20 and constriction regions 21 that are present in the microfluidic channels of the microfluidic device 10. The shear forces that act upon the fat cells contained in the nanofat 110 are transformed or otherwise activated in response to the shear force to enrich the fraction of mesenchymal stem cells and Muse cell subpopulations. The nanofat 110 is flowed through the microfluidic device 10 for a number of cycles (e.g., >25) as seen in operation 230. The sheared nanofat 110 is then collected in operation 240. The sheared nanofat 110 may optionally be subject to a filtering operation as illustrated in FIG. 1B. In one preferred aspect of the invention, the sheared nanofat 110 is then injected and/or applied to the subject. For example, the sheared nanofat 110 may be injected back into the subject's body at a different location from wherein the lipoaspirate was obtained. The particular site of application of the sheared nanofat 110 may vary depending on the application. For example, for wound healing applications, the sheared nanofat 110 is applied to a wound site. This may include intra-dermal, subdermal, or even topical application. For aesthetic sculpting (e.g., volumizing applications) applications, the sheared nanofat 110 may be injected or applied in combination with other autologous tissue such as, for example, a fat graft and injected at the desired location site on the body. This may include the subject's facial region, buttocks, breast, or any other soft-tissue location that may benefit from a lipofilling effect. In one aspect, the sheared nanofat 110 is centrifuged, and the resulting stem cell pellet, non-enzymatically obtained SVF, may be injected at the site of needed tissue regeneration, for example myocardium that is necrotic or of decreased function, or at the site of a poorly functioning or injured nerve that is exhibiting poor or delayed regeneration.

For experiments described herein, two versions of the microfluidic device 10 were created. A first version is referred to as "v2" in which case the fourth or final stage has a constriction width of 250 µm. A second version of the microfluidic device 10 is referred to as "v4" and used a fourth or final stage with a constriction width of 500 µm. The height for both versions of the device was 300 µm.

Experiments were conducted on standard lipoaspirate (i.e., macrofat) as well as nanofat prepared by passing macrofat between two syringes in a repeated manner.

Lipaspriate samples are from human subjects undergoing routine liposuctions procedures at UCI hospital (IRB #2015-2181) and washed thoroughly with phosphate buffered saline (PBS) prior to processing. For a control, macrofat was processed in the traditional manner using collagenase. Nanofat-derived stromal vascular fraction (SVF) is known to contain significantly reduced proportion of viable cells compared to standard lipoaspirate. Conversely, nanofat-derived SVF is known to have a greater proportion of mesenchymal stem cells (MSCs), adipose derived stem cells (ADSCs), endothelial progenitor cells (EPCs), and Muse cells. It was postulated that the amount of stress that is applied to cells directly correlates with stem-like properties.

Figure 3:
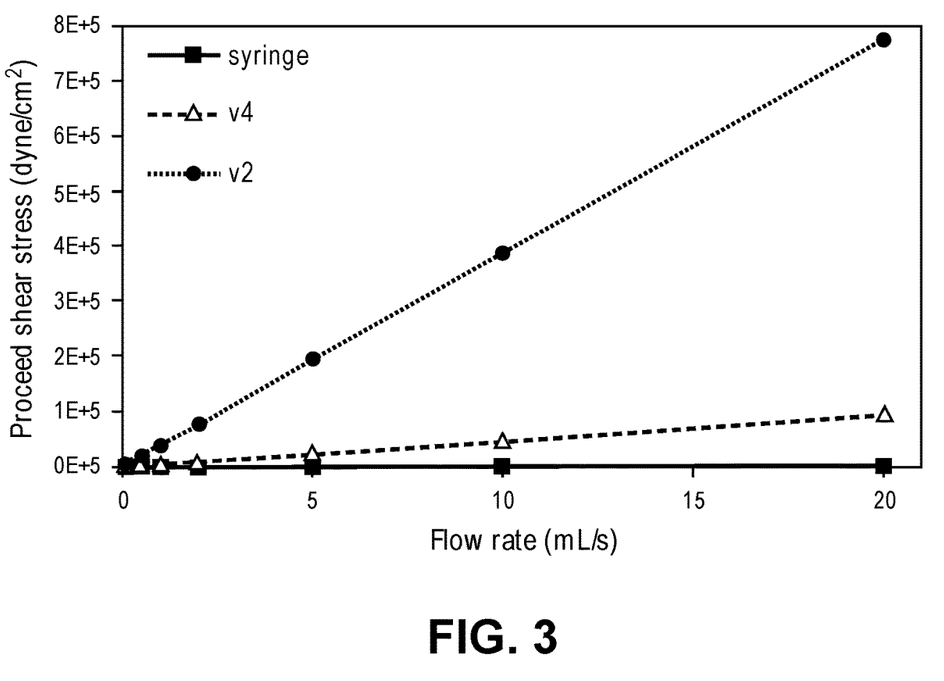
FIG. 3 illustrates a graph of the shear stress imparted on cells using the v2 and v4 versions of the microfluidic devices. Also illustrated is the stress imparted by the syringe alone for comparison purposes.

FIG. 3 illustrates the shear stress imparted on cells using the v2 and v4 microfluidic devices 10. Also illustrated is the stress imparted by the syringe. Processing was conducted at a flow rate of 12.5 ml/min. Table 1 below illustrates the results.

TABLE 1

|  | v4 | v2 |
| --- | --- | --- |
| Minimum dimension | 500 µm | 250 µm |
| Average velocity (m/s) | 1.06 | 4.24 |
| Average shear stress (dynes/cm$^2$) | 8,049 | 64,395 |

Figure 4:
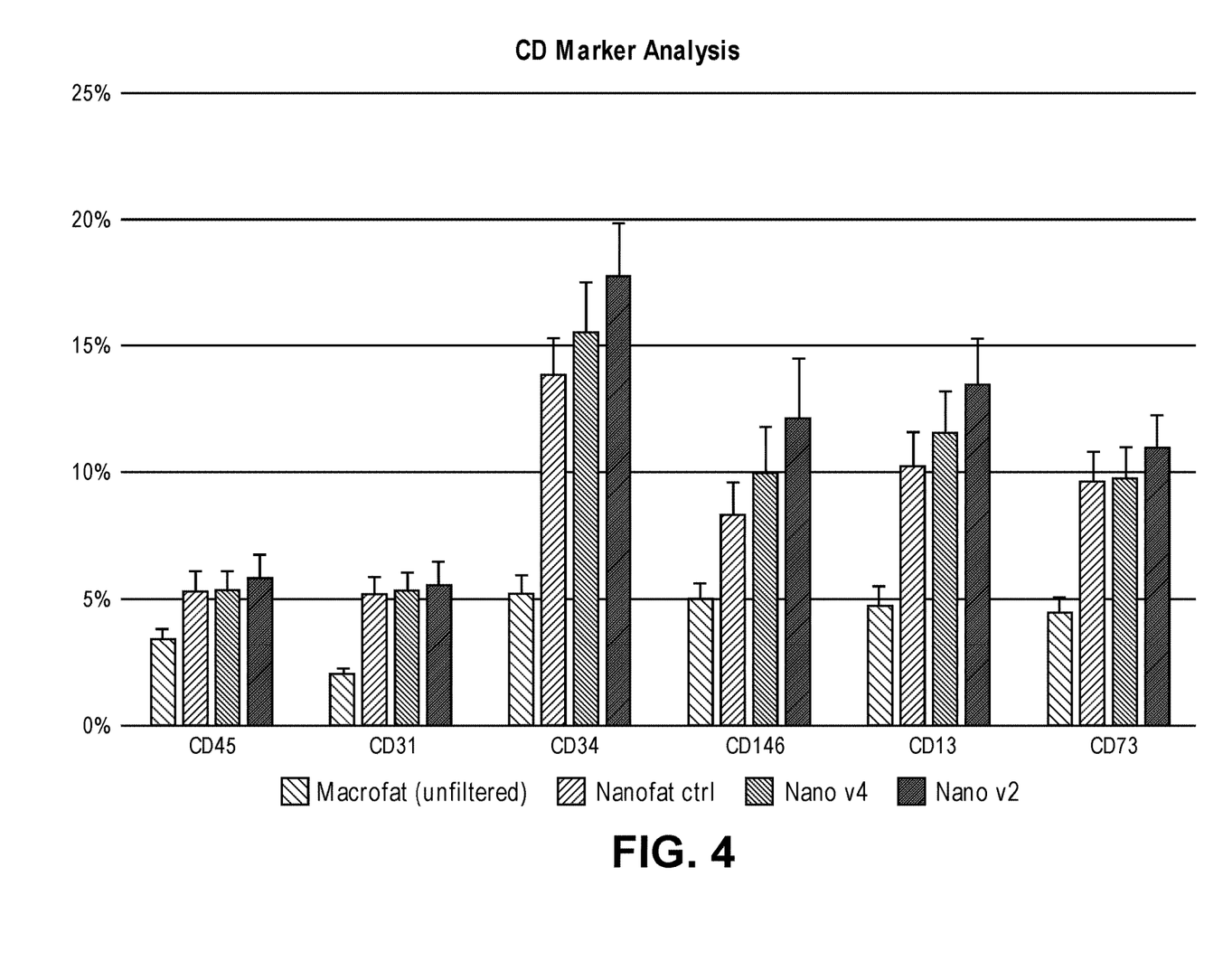
FIG. 4 illustrates a histogram showing the effects of shear stress on filtered nanofat-processed lipoaspirate CD marker expression (n=10) for macrofat samples, nanofat control samples, and nanofat samples that were run through the v2 and v4 microfluidic devices. There is a stress-dependent enrichment in CD markers associated with mesenchymal stem cell activity.
Figure 5:
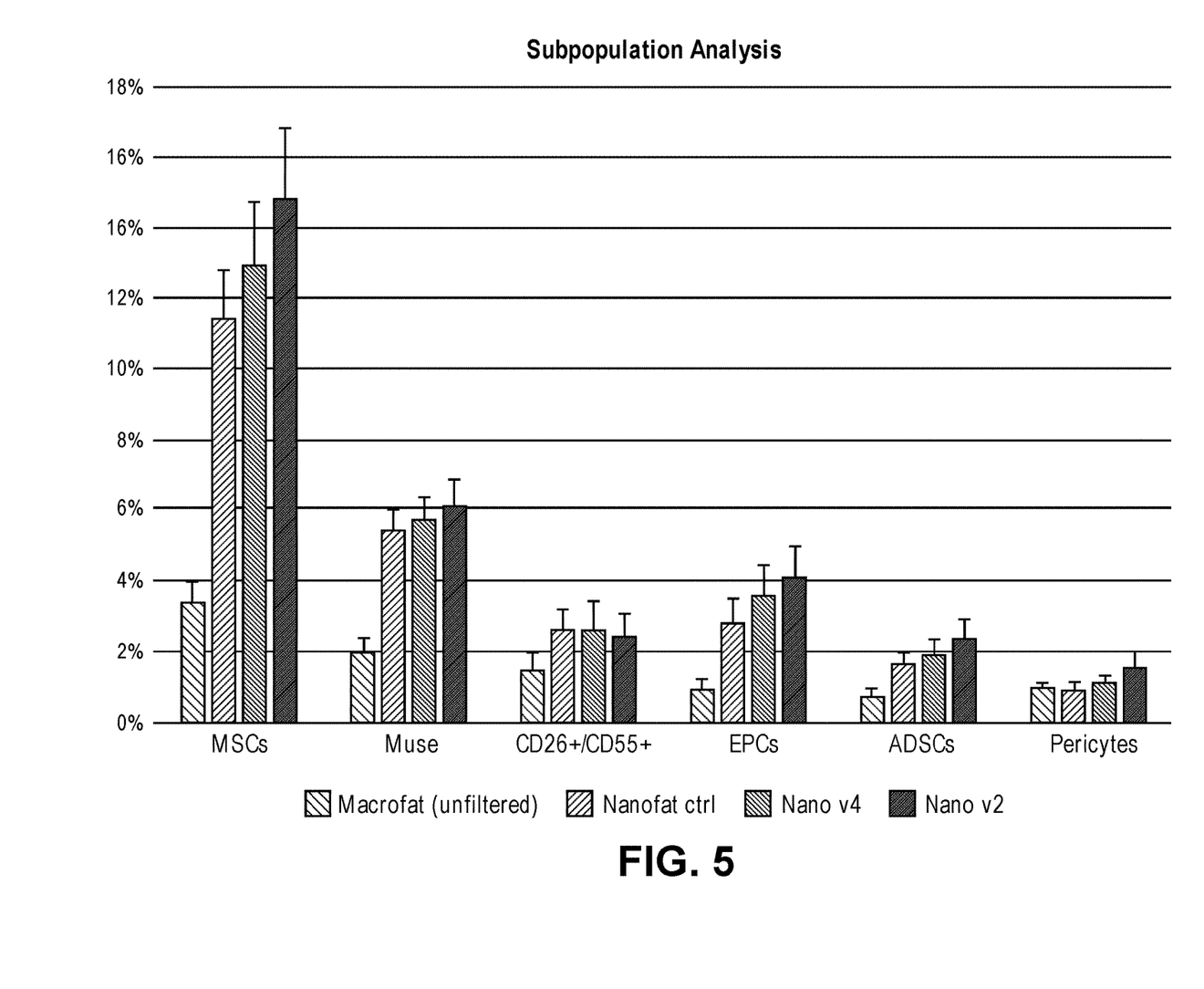
FIG. 5 illustrates a histogram showing the effects of shear stress on filtered nanofat-processed lipoaspirate subpopulation enrichment (n=10). There is a stress-dependent enrichment in mesenchymal stem cell and Muse cell subpopulations. CD26+/CD55+ subpopulations are enriched in the processed samples as well, but not in the dose-dependent fashion observed with the other subpopulations.

Experiments were conducted on fat (standard lipoaspirate) that was obtained from a single patient that was washed with PBS until golden in color. Nanofat was prepared by passing standard lipoaspirate between two syringes at a rate of 20 ml/second. Once emulsified, the tissue was passed through a standard kitchen strainer. The filtrate was collected and one portion set aside as a positive control, while two samples were passed through each microfluidic device for thirty (30) passes at 12.5 ml/min. FIG. 4 illustrates the analysis results for the presence of a variety of "sternness" markers. FIG. 5 illustrates stem cell subpopulations associated with improved wound healing. In particular, FIG. 5 illustrates a histogram showing the effects of shear stress on filtered nanofat-processed lipoaspirate subpopulation enrichment (n=10). There is a stress-dependent enrichment in mesenchymal stem cell and Muse cell subpopulations.

The control and emulsified lipoaspirate were then processed for SVF. A 0.1% enzymatic digestion solution was prepared by combining type I collagenase with PBS which was then sterilized using a 0.22 µm vacuum filter. A 1:1 volume of collagenase solution to lipoaspirate was incubated in a water bath at 37° C. for 30 minutes, swirling intermittently. An equal volume of control medium (Dulbecco's Modified Eagle Medium, 10% fetal bovine serum, 500 IU Penicillin, 500 µg Streptomycin) was then added to neutralize enzymatic activity and the mixture was allowed to separate for at least 10 minutes. The liquid infranatant layer containing the SVF was isolated, filtered through a 100 µm cell strainer, and centrifuged at 1800 rpm for 8 minutes. Each pellet was then resuspended in red blood cell lysis buffer (15.5 mM $NH_4Cl$, 1 mM $KHCO_3$, and 0.01 mM EDTA) for 5 minutes to minimize erythrocyte contamination. After the addition of 5 mL control medium, the suspensions were centrifuged one final time. The aqueous portions were removed by aspiration after each centrifugation step. The resulting pellets were then resuspended in control media and subjected to staining and analysis. Macrofat is standard lipoaspirate (control group) that was digested with collagenase for SVF isolation as described above.

A variety of research indicates that CD34 serves as a universal marker for stem cell activity. The presence of this marker combined with the absence of CD45 denotes a broad definition for mesenchymal sternness. Various other markers including CD13, CD73 and CD146 are associated with multipotentiality of the mesenchyme. The presence or absence of CD31 allows for the analysis of endothelial progenitor cells versus other constituents of the stromal vascular fraction. DPP4+ (CD26)/CD55+ cells have recently been identified as the crucial stem cell subtype associated with diabetic wound healing. Finally, the presence of both markers SSEA-3 combined with CD13 connote a pluripotent stem cell population.

All the recovered cell pellets were counted via LunaSTEM automated cell counter followed by the absolute cell count function using a MACSQuant flow cytometer. Nanofat groups resulted in a ~4-fold decrease in cell count (FIG. 6A) when compared to macrofat. Viability, however, was similar among the macrofat, nanofat control, v2, and v4 samples. For flow cytometry analysis, each sample was stained with the following combination of stains: (1) multipotency CD13-APC-Vio770, CD31-FITC, CD34-PerCP-Vio700, CD45-VioBlue, CD73-PE and CD146-APC; (2) pluripotency: CD45-VioBlue, CD31-FITC, CD34-PerCP-Vio700, CD13-APC-Vio770, SSEA-3-PE; (3) wound healing: CD31-FITC, CD34-PerCP-Vio700, CD45-VioBlue, CD26-PE, CD55-APC. For each sample, at least 100,000 cells per condition were aliquoted into FACS tubes and washed with cold PBS. The tubes were centrifuged at 1,500 RPM for 5 minutes and the supernatant discarded. The cell pellets were resuspended in 100 µm FACS running buffer followed by the addition of the combination stains listed above and incubated in cold, dark conditions for 15 minutes. Four ml of cold running buffer was then added to each tube to resuspended the pellet and dilute the antibodies. The tubes were spun once more at 1,500 RPM for 5 minutes. The supernatant was discarded and the pellets were resuspended in a final volume of 300 ml of running buffer for flow cytometry analysis.

Figure 6A:
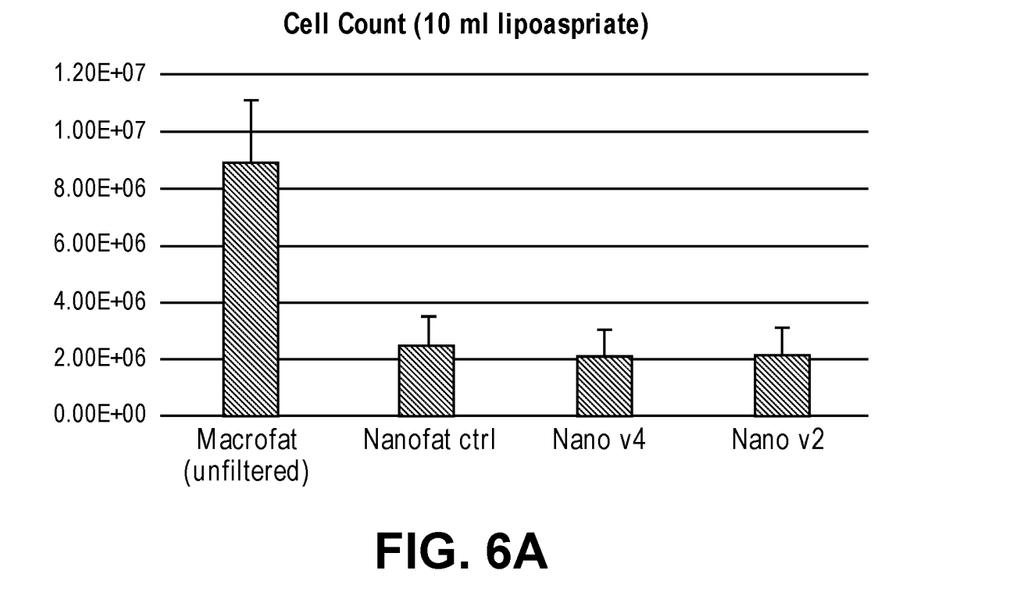
FIG. 6A illustrates a graph showing the effects of shear stress on cell count for the unfiltered macrofat sample, the nanofat control sample, the nanofat run through the v4 device, and nanofat run through the v2 device.
Figure 6B:
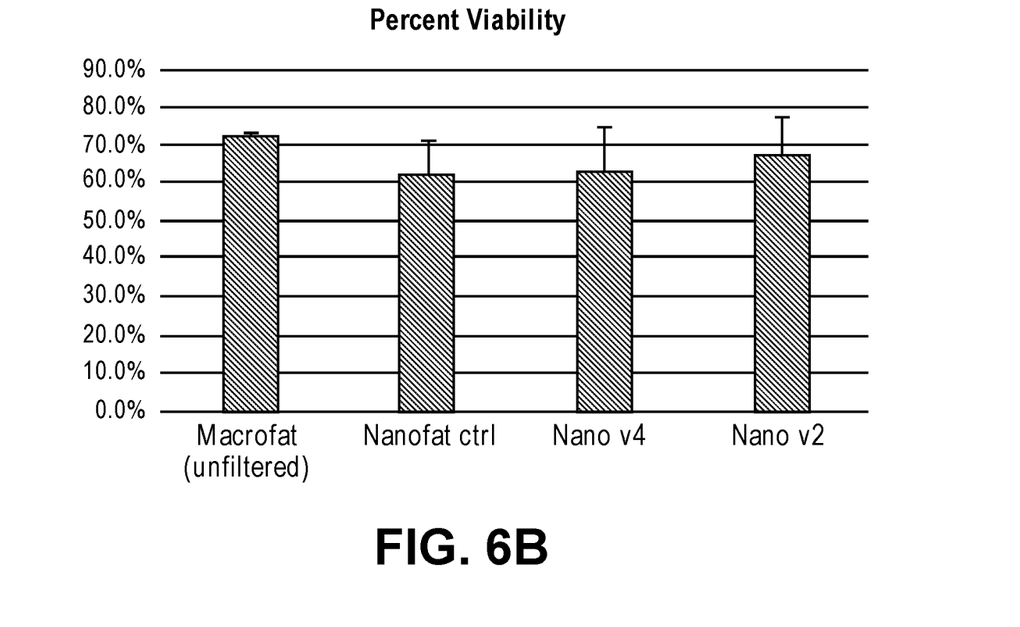
FIG. 6B illustrates a graph showing the effects of shear stress on viability for the unfiltered macrofat sample, the nanofat control sample, the nanofat run through the v4 device, and nanofat run through the v2 device.

FIG. 4 illustrates the phenotype marker results. One can see that for most markers there is a notable increase in expression for those samples run through the v4 and v2 devices. FIG. 5 illustrates subtype analysis that demonstrates that the primary cells upregulated in this emulsified tissue are mesenchymal stem cells, adipose-derived stem cells, and endothelial progenitor cells. In summary, nanofat processing yields significantly fewer cells than unprocessed fat, but v2 and v4 processing yields viability similar to that of nanofat and macrofat. Further, there is a dose-dependent (dose in this context refers to shear forces) relationship between the amount of stress applied to the fat and stem cell induction (v2 (~64,395 dynes/cm$^2$) shows more induction as compared to v4 (~8,049 dynes/cm$^2$). FIG. 6A illustrates the effects of shear stress on cell count for the unfiltered macrofat sample, the nanofat control sample, the nanofat run through the v4 device, and nanofat run through the v2 device. FIG. 6B illustrates the effects of shear stress on viability for the unfiltered macrofat sample, the nanofat control sample, the nanofat run through the v4 device, and nanofat run through the v2 device. As seen in FIG. 6A, the nanofat processing results in about a four-fold decrease in cell count. Moreover, as seen in FIG. 6A, cell count numbers for fat processing using the microfluidic device is nearly identical to the cell count for fat processing using traditional nanofat processing techniques. FIG. 6B illustrates that mechanical processing does not significantly affect cellular viability.

While embodiments of the present invention have been shown and described, various modifications may be made without departing from the scope of the present invention. The invention, therefore, should not be limited except to the following claims and their equivalents.

What is claimed is:

1. A method of processing a lipoaspirate sample comprising:
   mechanically processing the lipoaspirate sample to generate nanofat;
   inputting the nanofat into a microfluidic device comprising a plurality of serially arranged stages comprising one or more microfluidic channels having a plurality of expansion and constriction regions extending along the length of the one or more microfluidic channels and formed in channel walls of the one or more microfluidic channels and connected to one another in smooth curves, wherein each subsequent stage of the plurality has an increasing number of microfluidic channels of decreasing dimensions;
   flowing the nanofat through the plurality of serially arranged stages in a plurality of cycles to generate sheared nanofat; and
   collecting the sheared nanofat after flowing through the plurality of serially arranged stages.

2. The method of claim 1, further comprising filtering the sheared nanofat through a filter module.

3. The method of claim 1, further comprising injecting the sheared nanofat at an application site on a mammal.

4. The method of claim 3, wherein the application site comprises a wound.

5. The method of claim 3, wherein the application site comprises a volumizing site.

6. The method of claim 1, further comprising injecting the sheared nanofat in combination with other autologous tissue at an application site on a mammal.

7. The method of claim 6, wherein the sheared nanofat is combined with a fat graft.

8. The method of claim 6, wherein the application site comprises a wound.

9. The method of claim 6, wherein the application site comprises a volumizing site.

10. The method of claim 1, further comprising applying the sheared nanofat to the surface of a mammalian tissue.

11. The method of claim 1, wherein the nanofat is created by passing the lipoaspirate sample through a filter or strainer.

12. The method of claim 1, wherein the nanofat is created by passing the lipoaspirate sample back and forth between two syringes.

13. The method of claim 1, further comprising washing the lipoaspirate sample with saline or a buffer solution.

14. The method of claim 1, wherein the nanofat is flowed through the plurality of serially arranged stages in more than 25 cycles.

15. The method of claim 1, wherein a last stage of the plurality of stages has a minimum distance within the range of about 200 µm to about 600 µm.

16. The method of claim 1, wherein the sheared nanofat has an enriched amount of stem cells contained therein.

17. The method of claim 1, wherein the nanofat is pumped through the plurality of serially arranged stages.

18. A method of transforming fat cells from a subject comprising
   mechanically processing a lipoaspirate sample obtained from the subject sample to generate nanofat;
   inputting the nanofat into a microfluidic device comprising a plurality of serially arranged stages comprising one or more microfluidic channels having a plurality of expansion and constriction regions extending along the length of the one or more microfluidic channels and formed in channel walls of the one or more microfluidic channels and connected to one another in smooth curves, wherein each subsequent stage of the plurality has an increasing number of microfluidic channels of decreasing dimensions;
   flowing the nanofat through the plurality of serially arranged stages in a plurality of cycles to generate sheared nanofat; and
   collecting the sheared nanofat after flowing through the plurality of serially arranged stages.

* * * * *